United States Patent [19]

Töpfl

[11] Patent Number: 4,656,273
[45] Date of Patent: Apr. 7, 1987

[54] PROCESS FOR PRODUCING SULFONYLUREAS

[75] Inventor: Werner Töpfl, Dornach, Switzerland

[73] Assignee: Ciba-Geigy Corporation, Ardsley, N.Y.

[21] Appl. No.: 809,462

[22] Filed: Dec. 16, 1985

Related U.S. Application Data

[63] Continuation-in-part of Ser. No. 629,134, Jul. 9, 1984, abandoned.

[51] Int. Cl.⁴ .................. C07D 251/16; C07D 251/42; C07D 239/69; C07D 249/12
[52] U.S. Cl. .................................. 544/211; 544/212; 544/49; 544/321; 544/331; 544/332; 548/207; 548/262; 548/265; 548/268; 548/266
[58] Field of Search ............... 544/212, 321, 331, 332, 544/211, 49; 548/262, 263, 265, 266, 268, 207

[56] References Cited

U.S. PATENT DOCUMENTS 4,158,776 5/1985 Meyer et al. ......................... 544/207
4,465,505 8/1984 Wolf ......................................... 71/93

FOREIGN PATENT DOCUMENTS 0044807 1/1982 European Pat. Off.
0044808 1/1982 European Pat. Off.
0044809 1/1982 European Pat. Off.
0070802 1/1983 European Pat. Off.
0094790 11/1983 European Pat. Off.

*Primary Examiner*—John M. Ford
*Attorney, Agent, or Firm*—Edward McC. Roberts; Kevin T. Mansfield

[57] ABSTRACT

There is described a novel process for producing sulfonylureas of formula I

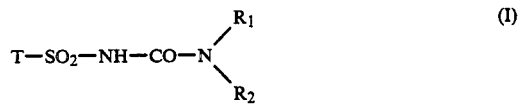

wherein
$R_1$ is hydrogen or alkyl,
$R_2$ is

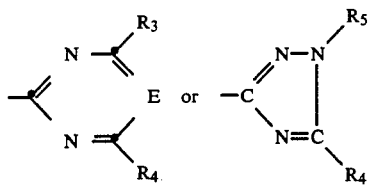

$E$ is $=N-$ or $=CH-$,
$R_3$ is alkyl, alkoxy or halogen,
$R_4$ is alkyl, cycloalkyl, alkoxy, halogen, alkoxy-alkyl, halo-alkyl or halo-alkoxy,
$R_5$ is hydrogen or alkyl,
$T$ is a substituted phenyl group

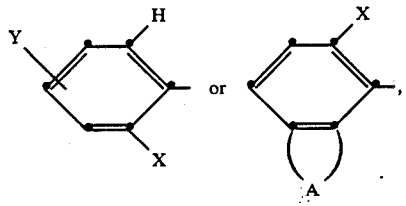

$Y$ is hydrogen or halogen,
$X$ is hydrogen, halogen, alkyl, halo-alkyl, alkenyl, halo-alkenyl, alkynyl, alkoxy, halo-alkoxy, alkylthio, alkylsulfinyl, alkylsulfonyl, halo-alkylthio, alkylsulfonyloxy, phenylsulfonyloxy, phenylsulfonyloxy mono- or polysubstituted by alkyl, or is di-alkylsulfamoyl, and
$A$ is a bridge member which has 3 or 4 atoms and which contains 1 or 2 hetero atoms, selected from the group consisting of oxygen, sulfur and nitrogen, the said process comprising reacting a silfonamide of the formula II

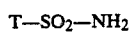

$$T-SO_2-NH_2 \qquad (II),$$

in the presence of a base, with diphenyl carbonate to form a salt of a phenyl carbamate converting this salt into the free phenyl carbamate and reacting this further with an amine. Sulfonylureas are herbicidally effective compounds.

18 Claims, No Drawings

PROCESS FOR PRODUCING SULFONYLUREAS

This is a continuation-in-part of my U.S. patent application Ser. No. 629,134, filed July 9, 1984, now abandoned.

The present invention relates to a process for producing sulfonylureas of formula I

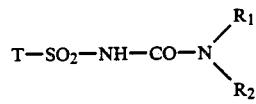

$R_1$ is hydrogen or $C_1$-$C_4$-alkyl,
$R_2$ is

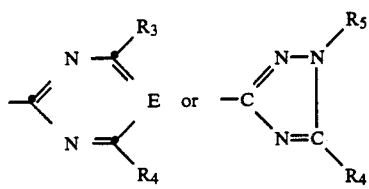

E is =N or =CH—,
$R_3$ is $C_1$-$C_4$-alkyl, alkoxy or halogen
$R_4$ is $C_1$-$C_4$-alkyl, $C_3$-$C_6$-cycloalkyl, $C_1$-$C_4$-alkoxy, halogen, $C_1$-$C_4$-alkoxy-$C_1$-$C_4$-alkyl, halo-$C_1$-$C_4$-alkyl or halo-$C_1$-$C_4$-alkoxy,
$R_5$ is hydrogen or $C_1$-$C_4$-alkyl,
T is

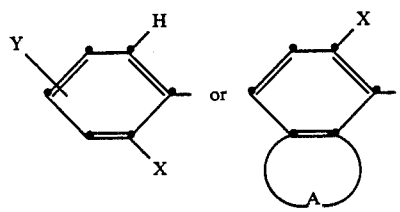

Y is hydrogen or halogen,
X is hydrogen, halogen, nitro, $C_1$-$C_4$-alkyl, halo-$C_1$-$C_4$-alkyl, $C_2$-$C_4$-alkenyl, halo-$C_2$-$C_4$-alkenyl, $C_2$-$C_4$-alkynyl, $C_1$-$C_4$-alkoxy, halo-$C_1$-$C_4$-alkoxy, $C_1$-$C_4$-alkoxy-$C_1$-$C_4$-alkoxy, $C_1$-$C_4$-alkylthio, $C_1$-$C_4$-alkylsulfinyl, $C_1$-$C_4$-alkylsulfonyl, halo-$C_1$-$C_4$-alkylthio, $C_1$-$C_4$-alkylsulfonyloxy, phenyl, unsubstituted phenylsulfonyloxy or phenylsulfonyloxy mono- or polysubstituted by $C_1$-$C_4$-alkyl, or is $C_1$-$C_4$-dialkylsulfamoyl, and
A is an unsubstituted or substituted bridge member which has 3 or 4 atoms and which contains 1 or 2 hetero atoms, selected from the group consisting of oxygen, sulfur and nitrogen and forms, together with the carbon atoms binding it, a nonaromatic 5- or 6-membered heterocycle, two oxygen atoms being separated by at least one carbon atom, and oxygen and sulfur atoms being linked together only when the sulfur atoms are present as —SO— or —SO— groups,
said process comprising the steps of reacting a sulfonamide of formula II

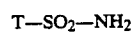

with diphenyl carbonate in the presence of a base, in the absence of water, in an aprotic solvent at 0°–30° C., to form a salt of a phenyl carbamate of formula III

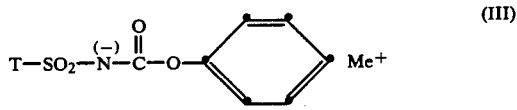

wherein Me+ is a cation of sodium or of potassium or of a tertiary amine, subsequently, without isolating the phenyl carbamate salt of formula III adding sufficient anhydrous acid thereto to convert this salt into the free phenyl carbamate of formula IIIa

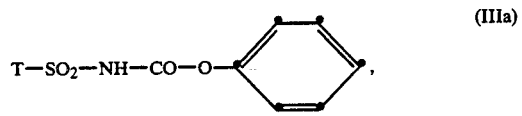

and reacting the phenyl carbamate of formula IIIa further with an amine of formula IV

at 20°–150° C., to give the sulfonylurea of formula I.

Sulfonylureas of the formula I exhibit an excellent herbicidal action, and can therefore be advantageously used in herbicidal compositions. Sulfonylureas of the formula I and their production and use are described for example in the U.S. Pat. Nos. 4,127,405, 4,169,719 and 4,238,621, in the European Patent Application No. 83810005.5 and in the South African Patent Specification No. 4874/81.

It is known that p-toluenesulfonyl-butylurea can be produced from p-toluenesulfonyl-phenylcarbamate and butylamine [Jap. Patent Application No.: 33-13484, C.A. 1962/I 7218 g].

It is also known that there is formed from the sodium salt of p-toluenesulfonamide and diphenyl carbonate the sodium salt of p-toluenesulfonylphenyl carbamate, from which N-p-toluenesulfonylphenyl carbamate can be liberated and isolated by the addition of an acid Jap. Patent Application No.: 33-13483, C.A. 1962/I 7218 f].

In the aforementioned production process, the hydrolysis-sensitive sulfonylphenyl carbamate is isolated, as an intermediate, by a complicated procedure (extraction with ether) in the presence of water. The yield of phenyl-p-toluenesulfonyl carbamate is only 50% of theory. The yield of the final product, 1-(p-toluenesulfonyl)-3-butylurea, is 47% of theory, relative to the employed p-toluenesulfonamide. The production of sulfonylureas of the formula I using this method is not of commercial interest on account of the disadvantages mentioned.

According to the process of the present invention, there are preferably used sulfonamides of the formula IIa

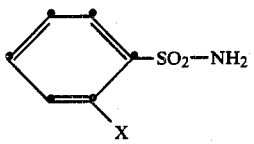
(IIa)

in which X has the meaning defined in the foregoing.

Suitable starting products for carrying out the inventive process are for example the following sulfonamides of the formula II:
2-fluorobenzenesulfonamide,
2-chlorobenzenesulfonamide,
2-nitrobenzenesulfonamide,
2-methylbenzenesulfonamide,
2-trifluoromethylbenzenesulfonamide,
2-methoxybenzenesulfonamide,
2-difluoromethoxybenzenesulfonamide,
2-(2'-chloroethoxy)-benzenesulfonamide,
22-(2'-methoxyethoxy)-benzenesulfonamide,
2-n-propylthiobenzenesulfonamide,
2-methylsulfonylbenzenesulfonamide,
2-n-propylsulfonylbenzenesulfonamide,
2-methylsulfonyloxybenzylsulfonamide,
2-n-propylsulfonyloxybenzenesulfonamide,
2-dimethylsulfamoylbenzenesulfonamide, and
2,3-dihydrobenzofurano-7-ylsulfonamide.

If Y is hydrogen in the case of the employed arylsulfonamide of the formula II, preferred amines of the formula IV according to the process of the invention are the following:
2-amino-4-methyl-6-methoxy-s-triazine,
2-amino-4-methyl-6-methoxypyrimidine,
2-amino-4-methyl-6-difluoromethoxypyrimidine,
2-amino-4,6-dimethoxypyrimidine,
2-amino-4,6-dimethoxy-s-triazine,
2-amino-4,6-dimethylpyrimidine,
2-amino-4-methoxy-6-ethoxy-s-triazine,
2-amino-4-dimethylamino-6-methoxy-s-triazine,
2-amino-4-cyclopropyl-6-methoxy-s-triazine,
2-amino-4-methoxy-6-methoxymethylpyrimidine,
2-amino-4-methoxy-6-chloropyrimidine,
2-amino-4-methoxy-6-chloromethylpyrimidine,
3-amino-1,5-dimethyl-1,2,4-triazole, and
3-amino-5-methoxy-1-methyl-1,2,4-triazole.

Several variants are possible for carrying out the process according to the invention. According to the first variant, the sulfonamide of the formula II is firstly converted with the equivalent amount of a base into an alkali salt, for example the sodium or potassium salt, or into a salt of a suitable tertiary amine. The subsequent processing of the reaction product is such that the resulting salt is finally in the form of a solution or of a suspension in an aprotic solvent, with the exclusion of water.

The subsequent reactions according to the process of the invention are then carried out in an aprotic solvent in the absence of water.

Suitable aprotic solvents are for example: acetonitrile, tetrahydrofuran, dioxane, 1,2-dimethoxyethane, dimethylformamide, N,N-dimethylacetamide or N-methylpyrrolidone, or mixtures of these solvents with one another. Particularly suitable as solvent is acetonitrile.

There are several possibilities available for converting the sulfonamide of the formula II into a salt thereof.

To produce the alkali salt, the sulfonamide of the formula II can firstly be reacted with an alkali metal hydroxide in a solvent, for example alcohol; the resulting alkali metal salt can then be obtained, after the addition of a second solvent, for example toluene, and after removal of the solvent by evaporation, in the form of an anhydrous residue. This can if required be subsequently dried in vacuo.

Suitable alkali metal hydroxides are sodium and potassium hydroxides. Potassium hydroxide is preferred as the alkali metal hydroxide.

The sodium or potassium salt of the sulfonamide of the formula II can be obtained in an analogous manner also by reaction of the free sulfonamide with a sodium or potassium alcoholate in an alcoholic solution. The resulting alkali metal salt of the sulfonamide of the general formula II is then suspended, after drying if required, in an aprotic solvent.

The tertiary ammonium salts of the sulfonamides of the general formula II can be produced, in the form of anhydrous solutions, by mixing together equivalent amounts of the sulfonamide and of a suitable tertiary amine in an aprotic solvent, and can be directly further used. The tertiary amines need to have moreover a basicity sufficient for salt formation with the sulfonamide. Suitable tertiary amines for salt formation are for example: 1,8-diazabicyclo(5,4,0)-undec-7-ene or 1,5-diazabicyclo(4,3,0)non-5-ene. These salt-forming tertiary amines are commercially obtainable, and can be recovered after the reaction.

The thus resulting suspension or solution of the alkali metal salt or tertiary ammonium salt of the sulfonamide can be converted according to the process of the invention by several methods into the corresponding sulfonylurea. According to a preferred method which can be carried out in a single reaction vessel, the salt suspended or dissolved in an aprotic solvent is mixed with an equivalent amount of diphenyl carbonate, and the mixture is stirred at 0°–30° C. for 1 to 12 hours, during which time the desired reaction to the sulfocarbamate salt occurs. The total amount of sulfocarbamate is liberated therefrom by the addition of an equivalent amount of a suitable anhydrous acid, for example methanesulfonic acid or hydrogen chloride, optionally dissolved at 0°–30° C. Methanesulfonic acid is preferred as the anhydrous acid. The use of hydrogen chloride dissolved in acetonitrile is likewise preferred. The resulting sulfocarbamate solution is reacted with an equivalent amount of the heterocyclic amine to give the sulfonylurea, the temperature of the reaction mixture being increased from initially 20° C. up to the boiling point of the solvent, up to a maximum however of 150° C. The acid and the heterocyclic amine can also be added simultaneously. According to a further method, the heterocyclic amine is converted in a second reaction vessel, in an aprotic solvent, by the addition of an acid into the corresponding salt and is used as such. The suspended or dissolved sulfocarbamate salt is then added to the suspended or dissolved amine salt between room temperature and the boiling point of the solvent. After the carrying out of the addition of the sulfocarbamate, the reaction mixture is heated, as described in the foregoing, until the reaction is completed.

According to yet a further, particularly preferred, variant for performing the process of the invention, the tert. amine used for salt formation with the sulfonamide is added dropwise, with the exclusion of water, to a prepared mixture consisting of the sulfonamide, diphenyl carbonate and the aprotic solvent to thus form the phenyl carbamate salt. Further processing of this intermediate can be carried out by one of the methods already described.

The processing of the reaction mixture is performed most simply when the resulting sulfonylurea, on cooling to 0°–20° C., crystallises out in the pure form. The reaction product is then obtained, after filtration, subsequent washing and drying, in the pure state. After further processing of the mother liquor, the solvent, the phenol formed as by-product as well as the optionally employed salt-forming amine can be separated in the pure form. In the case where the crystallisation of the sulfonylurea occurs to an unsatisfactory extent or not at all, it is possible to firstly evaporate off the solvent, to then optionally remove by distillation under reduced pressure the phenol formed as by-product, and to take up in the warm state the distillation residue in water and a solvent immiscible with water, for example toluene or cyclohexane, whereupon, on cooling, the sulfonylurea crystallises out from the solvent layer separated at elevated temperature. The product is filtered off, subsequently washed and then dried. By means of further processing by distillation of the mother liquor as well as of the separated aqueous layer, it is possible to isolate in the pure form both solvents, that is, the phenol formed as by-product, and also the optionally employed salt-forming amine. The yield, relative to the amount of sulfonamide used, is 50–80% of theory, over the two stages.

Compared with prior art processes, the process according to the present invention is advantageous in that it enables the hydrolysis-sensitive sulfonylphenyl carbamate to be produced with the exclusion of water and with an improved yield, and renders possible the carrying out of the entire reaction sequence in one reaction vessel.

According to the particularly preferred variant of the process of the invention, whereby the tertiary amine is introduced into a prepared mixture of the sulfonamide, the diphenylcarbonate and the solvent, it is possible to convert sulfonamides of the formula II substituted by sensitive groups, which do not yield under the conditions of other process variants a desirable product, into the corresponding sulfonylureas. Such sulfonamides are: 2-$C_1$-$C_4$-alkylsulfonyloxy, unsubstituted phenylsulfonyloxy or phenylsulfonyloxybenzenesulfonamides mono- or poly-substituted by $C_1$-$C_4$-alkyl, and 2-(2-halo-$C_1$-$C_4$ -alkoxy)benzenesulfonamides. By application of this particularly advantageous process variant, there are obtained in general yields of sulfonylureas which are higher than those obtained by other process variants.

EXAMPLE 1

Production of
N-[2-(N,N-dimethylsulfamoyl)-phenylsulfonyl]-N'-(4-chloromethyl-6-methoxypyrimidin-2-yl)-urea 26.4 g of 2-(N,N-dimethylsulfamoyl)-benzenesulfonamide (0.1 mol) are suspended in 100 ml of acetonitrile; 15.7 g of 1,8-diazabicyclo(5,4,0)undec-7-ene DBU (0.1 mol) are added, and the mixture is stirred for 1 hour at room temperature. There are then added 21.4 g of diphenyl carbonate (0.1 mol) and stirring is continued for 1 hour. After a standing time of 15 hours, 9.7 g of methanesulfonic acid (0.1 mol) are added dropwise in the cold state. There are afterwards added 17.3 g of 2-amino-4-chloromethyl-6-methoxypyrimidine (0.1 mol), and the suspension is refluxed for 1 hour, in the course of which there is firstly formed a solution from which, after a short time, the product precipitates in crystalline form. The reaction mixture is cooled and the product is filtered off under suction to thus obtain 32 g of slightly yellowish product; m.p. 214°–216° C. (decomp.); yield 70% of theory.

EXAMPLE 2

N-(2-Trifluoromethyl-phenylsulfonyl)-N'-(4-methoxy-6-methoxymethylpyrimidin-2-yl)-4'-urea 11.3 g (0.05 mol) of 2-trifluoromethylbenzenesulfonamide, 30 g of methanol and 5.8 g (0.05 mol) of K-tertbutylate are mixed in a flask with stirrer, and the solvent mixture is evaporated off in vacuo. The residue of 13.0 g, the K salt of sulfonamide, is suspended in 20 g of dioxane; 10.8 g (0.05 mol) of diphenyl carbonate are added and stirring is maintained for 12 hours at room temperature, in the course of which a suspension of the potassium salt of phenyl carbamate is formed. 1.8 g (0.05 mol) of HCl gas are then introduced, with stirring, into a cold solution of 8.5 g (0.05 mol) of 2-amino-4-methoxy-6-methoxymethylpyrimidine in 25 g of dioxane, whereupon the hydrochloride of the amine is formed as a suspension. To this suspension is subsequently added at the same temperature, during 30 minutes, the previously described suspension of the K salt of phenyl carbamate. The reaction mixture is held for a further 30 minutes at the refluxing temperature, and the dioxane is afterwards distilled off under normal pressure and the phenol in vacuo. The residue consisting of solid KCl and an oily organic part is diluted with 25 g of toluene at 60° C.; the KCl is dissolved with 20 g of water and layers are separated at 60° C. The product which recrystallises from the toluene layer in the cold state is filtered off, washed and then dried; yield: 15 g (71% of theory).

EXAMPLE 3

Production of
N-(2-methylsulfonyloxy-phenylsulfonyl-N'-(4-chloromethyl-6-methoxypyrimidin-2-yl) urea 25.1 g of 2-methylsulfonyloxy-benzenesulfonamide (0.1 mol), 21.4 g of diphenyl carbonate (0.1 mol) and 50 ml of acetonitrile are stirred together. To this prepared mixture are added dropwise at 0°–5° C. with stirring, in the course of 10 minutes, 15.7 g of 1,8-diazabicyclo-(5,4,0)-undec-7-ene DBU (0.1 mol), and the resulting solution is left to stand for 15 hours at room temperature. There are then added dropwise to the cooled solution 9.7 g of methanesulfonic acid (0.1 mol) at 0°–5° C. during 10 minutes with stirring. An addition of 17.3 g of 2-amino-4-chloromethyl-6-methoxypyrimidine (0.1 mol) is subsequently made, and the resulting suspension is refluxed for one hour, in the process of which a clear solution is formed. This is cooled and the product crystallising out is filtered off with suction. The yield is 29.5 g of product; m.p. 177°–179° C.; yield: 65% of theory.

EXAMPLE 4

Production of
N-(2,3-dihydro-benzo[b]furan-7-sulfonyl)-N'-(4-dimethylamino-6-methoxy-1,3,5-triazin-2-yl)-urea 8,0 g of 2,3-dihydro-7-sulfamoyl-benzo[b]furan (0,04 mol) and 7,1 g of diphenyl carbonate (0,04 mol) and 150 ml of acetonitrile are stirred together. To this suspension are added dropwise at 0°–5° C. 7,1 g (0,05 mol) of 1,8-diazabicyclo(5,4,0)-undec-7-ene DBU and the resulting solution is left to stand for 15 hours at room temperature. These are then added dropwise 4,4 g (0,045 mol) of methanesulfonic acid at 0°–5° C. An addition of 6,8 g (0,04 mol) of 2-amino-4-dimethylamino-6-methoxy-triazine is subsequently made and the resulting suspension is refluxed for two hours and the resulting turbid hot solution is filtered.

The filtered, clear solution is cooled and the crystalline product is filtered off with suction, washed with a mixture of acetone and ether and dried in vacuo.

The yield is 29,5 g of product, m.p. 177°–79° C.

EXAMPLE 5

Production of N-(2-Dioxy-3-methyl-3,4-dihydro-1,2-benzoxanthiin-8-yl-sulfonyl)-N'-(4-dimethylamino-6-methoxy-1,3,5-triazin-2-yl)-urea, melting point 216°–218° C.

The above-mentioned compound of formula I is prepared with 2,2-dioxo-3-methyl-3,4-dihydro-1,2-benzoxanthiin-8-yl-sulfonamid, as starting material of formula II by a procedure analogous to that of Example 4.

What is claimed is:

1. A process for producing a sulfonylurea of formula I

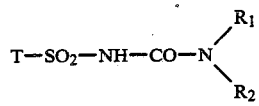  (I)

wherein
$R_1$ is hydrogen or $C_1$–$C_4$-alkyl,
$R_2$ is

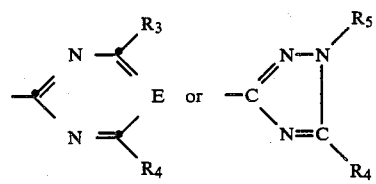

E is =N or =CH—,
$R_3$ is $C_1$–$C_4$-alkyl, alkoxy or halogen
$R_4$ is $C_1$–$C_4$-alkyl, $C_3$–$C_6$-cycloalkyl, $C_1C_4$-alkoxy, halogen, $C_1$–$C_4$alkoxy-$C_1$–$C_4$-alkyl, halo-$C_1$–$C_4$-alkyl or halo-$C_1$–$C_4$-alkoxy,
$R_5$ is hydrogen or $C_1$–$C_4$-alkyl,
T is

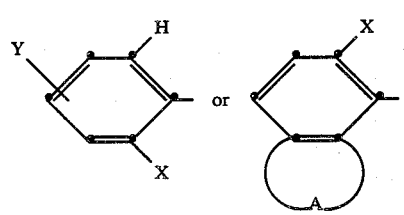

Y is hydrogen or halogen,
X is hydrogen, halogen, nitro, $C_1$–$C_4$-alkyl, halo-$C_1$–$C_4$-alkyl, $C_2$–$C_4$-alkenyl, halo-$C_2$–$C_4$-alkenyl, $C_2$–$C_4$-alkynyl, $C_1$–$C_4$-alkoxy, halo-$C_1$–$C_4$-alkoxy, $C_1$–$C_4$-alkoxy-$C_1$–$C_4$-alkoxy, $C_1$–$C_4$-alkylthio, $C_1$–$C_4$-alkylsufinyl, $C_1$–$C_4$-alkylsulfonyl, halo-$C_1$–$C_4$-alkylthio, $C_1$–$C_4$-alkylsulfonyloxy, phenyl, unsubstituted phenylsulfonyloxy or phenylsulfonyloxy mono- or poly-substituted by $C_1$–$C_4$-alkyl, or is $C_1$–$C_4$-dialkylsulfamoyl, and A is an unsubstituted bridge member which has 3 or 4 atoms and which contains 1 or 2 hetero atoms, selected from the group consisting of

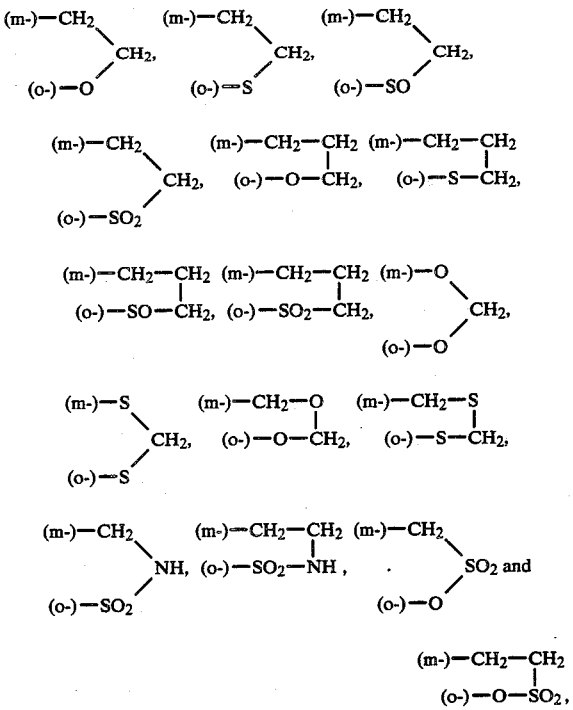

wherein (m-) and (o-) designate the metal and ortho positions relative to the sulfonylurea group on the aromatic ring to which said bridge member is fused, said process comprising the steps of reacting a sulfonamide of formula II $$T-SO_2-NH_2 \quad \text{(II)}$$

with diphenyl carbonate in the presence of a base, in the absence of water, in an aprotic solvent at 0°–30° C., to form a salt of a phenyl carbamate of formula III

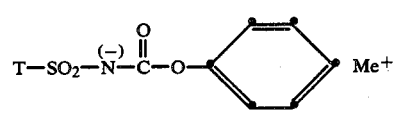 (III)

wherein Me+ is a cation of sodium or of potassium or of a tertiary amine, subsequently, without isolating the phenyl carbamate salt of formula III adding sufficient anhydrous acid thereto to convert this salt into the free phenyl carbamate of formula IIIa

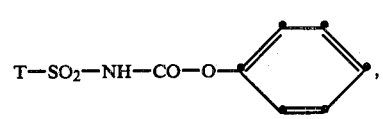 (IIIa)

and reacting the phenyl carbamate of formula IIIa further with an amine of formula IV

 (IV)

at 20°–150° C., to give the sulfonylurea of formula I.

2. A process of claim 1 wherein

X is hydrogen, halogen, $C_1$–$C_4$-alkyl, halo-$C_1$–$C_4$-alkyl, $C_2$–$C_4$-alkenyl, halo-$C_2$–$C_4$-alkenyl, $C_2$–$C_4$-alkynyl, $C_1$–$C_4$-alkoxy, halo-$C_1$–$C_4$-alkoxy, $C_1$–$C_4$-alkylthio, $C_1$–$C_4$-alkylsulfinyl, $C_1$–$C_4$-alkylsulfonyl, halo-$C_1$–$C_4$-alkylthio or $C_1$–$C_4$-dialkylsulfamoyl.

3. A process of claim 1, wherein the sulfonamide of formula II is selected from the group consisting of:
2-fluorobenzenesulfonamide,
2-chlorobenzenesulfonamide,
2-nitrobenzenesulfonamide,
2-methylbenzenesulfonamide,
2-trifluoromethylbenzenesulfonamide,
2-methoxybenzenesulfonamide,
2-difluoromethoxybenzenesulfonamide,
2-(2'-chloroethoxy)-benzenesulfonamide,
2-(2'methoxyethoxy)-benzenesulfonamide,
2-n-propylthiobenzenesulfonamide,
2-methylsulfonylbenzenesulfonamide,
2-n-propylsulfonylbenzenesulfonamide,
2-methylsulfonyloxybenzylsulfonamide,
2-n-propylsulfonyloxybenzenesulfonamide,
2-dimethylsulfamoylbenzenesulfonamide, and
2,3-dihydrobenzofurano-7-ylsulfonamide.

4. A process of claim 1, wherein Y is hydrogen.

5. A process of claim 1, wherein $R_1$ is hydrogen, and $R_2$ is 4-methyl-6-methoxy-s-triazin-2-yl, 4-methyl-6-methoxy-pyrimidin-2-yl, 4-methyl-6-difluoromethoxypyrimidin-2-yl, 4-methoxy-6-chloromethylpyrimidin-2-yl, 4,6-dimethoxy-s-triazin-2-yl, 4,6-dimethoxypyrimidin-2-yl, 4,6-dimethylpyrimidin-2-yl, 4-methoxy-6-ethoxytriazin-2-yl, 4-dimethylamino-6-methoxy-s-triazin-2-yl, 4-cyclopropyl-6-methoxy-s-triazin-2-yl, 4-methoxy-6-methoxymethylpyrimidin-2-yl, 4-methoxy-6-chloropyrimidin-2-yl, 1,5-dimethyl-1,2,4-triazol-3-yl or 5-methoxy-1-methyl-1,2,4-triazol-3-yl.

6. A process of claim 1, wherein the aprotic solvent is selected from the group consisting of acetonitrile, tetrahydrofuran, dioxane, 1,2-dimethoxyethane, dimethylformamide, N,N-dimethalacetamide and N-methylpyrrolidone.

7. A process of claim 6, wherein the aprotic solvent is acetonitrile.

8. A process of claim 1, wherein the phenyl carbamate is liberated from the phenyl carbamate salt by the addition simultaneously of the acid necessary for the purpose and the amine.

9. A process of claim 8, wherein the amine is added in the form of a salt.

10. A process of claim 1, wherein methanesulfonic acid or hydrogen chloride is used for liberating the sulfonylphenyl carbamate or for salt formation with the amine.

11. A process of claim 10, wherein the acid is methanesulfonic acid.

12. A process of claim 10, wherein the acid is hydrogen chloride dissolved in acetonitrile.

13. A process of claim 1, wherein the base is selected from the group consisting of sodium hydroxide, potassium hydroxide, sodium alcoholate, potassium alcoholate and a tertiary amine.

14. A process of claim 13, wherein the base is potassium hydroxide.

15. A process of claim 13, wherein the base is 1,8-diazabicyclo(5,4,0)undec-7-en or 1,5-diazabicyclo(4,3,0)non-5-ene.

16. A process of claim 15, wherein the base is added gradually to a prepared mixture consisting of the sulfonamide, the diphenyl carbonate and the aprotic solvent.

17. A process of claim 15, wherein the base, after the reaction sequence, is recovered and recycled.

18. A process of claim 17, wherein the reaction sequence is performed in a single reaction vessel.

* * * * *